United States Patent [19]

Simmonds et al.

[11] 4,401,652

[45] Aug. 30, 1983

[54] PROCESS FOR THE PREPARATION OF STROMA-FREE HEMOGLOBIN SOLUTIONS

[75] Inventors: Richard S. Simmonds, Landing, N.J.; Wells P. Owen, Nyack, N.Y.

[73] Assignee: Allied Corporation, Morris Township, Morris County, N.J.

[21] Appl. No.: 290,175

[22] Filed: Aug. 5, 1981

Related U.S. Application Data

[63] Continuation-in-part of Ser. No. 221,640, Dec. 31, 1980, abandoned.

[51] Int. Cl.$^3$ .............................................. A61K 35/14
[52] U.S. Cl. ................................ 424/101; 260/112 B; 424/177
[58] Field of Search ..................... 260/112 B; 424/101, 424/177

[56] References Cited

U.S. PATENT DOCUMENTS

| | | | |
|---|---|---|---|
| 3,864,478 | 2/1975 | Bonhard | 424/101 |
| 3,903,254 | 9/1975 | Dahlgren et al. | 260/112 B |
| 3,991,181 | 11/1976 | Doczi | 424/101 |
| 4,061,736 | 12/1977 | Morris et al. | 260/112 B |
| 4,064,118 | 12/1977 | Wong | 260/112 B |
| 4,136,093 | 1/1979 | Bonhard et al. | 260/112 B |

*Primary Examiner*—Sam Rosen
*Attorney, Agent, or Firm*—Webb, Burden, Robinson & Webb

[57] ABSTRACT

A process for preparing a stroma-free hemoglobin solution is provided. The process includes washing blood cells to remove noncellular components to obtain a mixture of erythrocytes and leukocytes. The leukocytes are removed from the mixture and the erythrocytes are lysed to form a mixture of stroma and hemoglobin. The stroma is precipitated from the hemoglobin by treating the stroma-hemoglobin mixture with a polyvalent cation; a polysulfate, and a polyvalent anion. The supernatant hemoglobin solution is separated and dialyzed to obtain a substantially pure hemoglobin solution.

15 Claims, No Drawings

PROCESS FOR THE PREPARATION OF STROMA-FREE HEMOGLOBIN SOLUTIONS

CROSS REFERENCE TO RELATED APPLICATIONS

This application is a continuation-in-part of copending U.S. application Ser. No. 221,640, filed Dec. 31, 1980, now abandoned.

BACKGROUND OF THE INVENTION

1. Field of the Invention

This invention relates to a process of preparing stroma-free hemoglobin solutions.

2. Description of the Prior Art

As is well-known, hemoglobin is the active oxygen transport compound in blood present in erythrocytes. It has long been desirable to obtain hemoglobin in substantially pure form free of stroma and blood enzymes for use as an "in vitro" diagnostic reagent and an "in vivo" blood substitute.

Stroma-free hemoglobin is known. However, complicated processes have been required in order to obtain stroma-free hemoglobin. One problem associated with the production of stroma-free hemoglobin is the conversion of hemoglobin to methemoglobin. This conversion occurs when the iron atom in the heme changes valence from $Fe^{++}$ to $Fe^{+++}$ due to oxidation. The methemoglobin does not function as a reversible oxygen transport mechanism as does hemoglobin. Thus care must be taken to prevent conversion of hemoglobin to methemoglobin in the purification process.

Several processes have been proposed for preparing stroma-free hemoglobin. Exemplary of such processes are those disclosed in "An Improved Stroma-Free Hemoglobin Solution" by Greenberg et al.; *Surgical Forum* V. 26, pp. 53–55 (1975); "Further Studies with Stroma-Free Hemoglobin Solution" by Rabiner et al.; *Annuals of Surgery*, pp. 615–622 (April 1970); "Acute Oxygen Supply by Infusion of Hemoglobin Solutions" by Bonhard; *Federation Proceedings* V. 34, No. 6, pp. 1466–1467 (May 1975); "Blood Substitute and Blood Plasma Expander Comprising Polyhemoglobin" by Bonsen et al., U.S. Pat. No. 4,001,401; and "Characteristics of Stroma-Free Hemoglobin Prepared by Crystallization" by DeVenuto et al.; *J. Lab. Clin. Med.*, pp. 509–516 (March 1977). None of these methods are satisfactory for large scale production of stroma-free hemoglobin, with reduced methemoglobin formation.

The present invention provides a method of producing stroma-free hemoglobin which is adapted to be used in large scale production. It does not require high speed centrifugation thereby facilitating large scale production. It provides a substantially pure stroma-free hemoglobin which is low in methemoglobin.

These and other advantages are attendant to the invention and will be more fully understood by the following disclosure thereof.

BRIEF DESCRIPTION OF THE INVENTION

The process for preparing a stroma-free hemoglobin solution includes washing blood cells to remove noncellular components to obtain a mixture of erythrocytes and leukocytes. The leukocytes are removed from the mixture and the erythrocytes are lysed to form a mixture of stroma and hemoglobin. The stroma is precipitated from the hemoglobin by treating the stroma-hemoglobin mixture with a polyvalent cation; a polysulfate, and a polyvalent anion. The supernatant hemoglobin solution is separated and dialyzed and sterile filtered to obtain a substantially pure hemoglobin solution.

DETAILED DESCRIPTION OF THE INVENTION

In obtaining stroma-free hemoglobin, the starting material may be either whole blood or packed red blood cells of humans, sheep, pigs, horses, cows or the like. They may be outdated. The preferred starting material is human while blood or packed red cells.

The whole blood or packed red cells are washed to remove plasma proteins and other noncellular blood components. The wash solution may be an isotonic or hypertonic aqueous solution in which the plasma proteins and other noncellular components are soluble and in which the cells are not lysed. An aqueous solution of $Na_2HPO_4$ and $NaCl$ has been used successfully.

The purpose of the initial wash is to remove enzymes, immunoglobins and other blood constituents which act as contaminants in hemoglobin solutions. Such contaminants may cause degradation of the hemoglobin and render it unsuitable for its intended uses. Typically the cells are mixed with wash solution and centrifuged either in a suitable container or in a continuous flow system. Equipment and techniques of performing this operation are well-known in the art.

During the washing process it is desirable to maintain the cells at about 5° C. to minimize the formation of methemoglobin during processing. Thus it is desirable to chill the centrifuge and associated apparatus along with the wash solution prior to processing of the cells. After centrifugation is complete, the supernatant wash solution is removed. This wash procedure is repeated, preferably at least one more time, in order to remove substantially all of the noncellular blood components of the whole blood or packed cells.

Subsequent to washing, the cells are processed so as to separate the remaining leukocytes from the erythrocytes. One method of separating leukocytes from the erythrocytes is to filter the cell mixture through a suitable absorbent which preferentially retains the leukocytes. Alternately one may filter the cell mixture through layers of mesh-like material such as nylon which is capable of retaining clumped white cells.

Upon collection of the substantially pure erythrocytes, the cells are lysed. Lysing can be accomplished by several known methods, however, it is preferred that the lysing be conducted rapidly and efficiently and for this reason ultrasonic or other mechanical disruption is preferred. In one method of ultrasonic disruption, an ultrasonic probe is equipped with a continuous flow cell through which the erythrocytes pass. During the disruption process, the disruption cell is cooled to avoid the generation of heat which tends to degrade the hemoglobin and convert it to methemoglobin. Preferably, the erythrocytes are pumped through the disruption cell at a speed which will result in a residual cell count that is less than or equal to 250,000/cu. millimeters in 1 to 3 passes. Excessive sonication may result in the formation of methemoglobin which is undesirable in the preparation of the hemoglobin solution in accordance with this invention.

Subsequent to cell lysis, the stroma is precipitated from the hemoglobin by treating the stroma-hemoglobin mixture with a polyvalent cation, a polysulfate, and a polyvalent anion. Polyvalent cations are those which are divalent or greater. The divalent cations useful in the practice of the invention are preferably calcium, magnesium, manganese, barium and tin and most preferably, calcium supplied in the form of a calcium chloride. Those polyvalent cations which are greater than divalent useful in the practice of the invention are iron, aluminum and the like and most preferably iron in the form of ferric chloride and aluminum in the form of aluminum ammonium sulfate. The polyvalent cation is preferably present at a level of 0.025 to 0.20 equivalents/liter of cells, and most preferably present at a level of 0.08 to 0.10 equivalents of divalent cation/liter of cells. The cation may be provided by calcium chloride, calcium bromide, magnesium chloride, manganese chloride, tin chloride, ferric chloride, aluminum ammonium sulfate and the like. When calcium chloride is used it is preferably used in a range of 2.5 grams/liter of cells to 20 grams/liter of cells.

The polysulfate used in the practice of the invention can be dextran sulfate, polyanetholsulfonate, heparin, and other similar polysulfates. The primary criteria for the polysulfate is that it be of high molecular weight and provide $SO_3H$ groups available for complexation with lipoprotein fragments. When dextran sulfate is used as a polysulfate in the practice of the invention, it is used at a concentration of 0.5 grams/liter of cells to 10 grams/liter of cells.

Polyvalent anions useful in the practice of the invention may be supplied by phosphate, oxalate, carbonate, citrate or the like and are preferably provided in a buffered from such as the sodium or potassium salt thereof, and more preferably the sodium salt. The most preferred polyvalent anion is supplied by $Na_2HPO_4$ at a level of 0.05 molar to 0.1 molar.

The treatment of the lysed erythrocytes with the polyvalent cation, the polysulfate and the polyvalent anion may be carried out at room temperature or colder. Each may be added either as a solid or in solution. Typically the polyvalent cation is added as an aqueous solution. Stirring should be as vigorously as possible, but not so rapidly as to cause excessive foaming and the incorporation of air into the mixture. The polysulfate is generally added as a powder which is sprinkled on the surface and mixed until complete dissolution occurs. The polyvalent anion which is preferably added subsequent to the other agents is typically added as a solid and mixed until all material is dissolved.

Subsequent to adding the precipitating agents to the stroma-hemoglobin mixture, the admixture is cooled. Both soluble and insoluble lipoprotein constituents including the stroma are complexed as a precipitate and removed by centrifugation. The supernatant liquid, which is the hemoglobin solution, is collected.

Each of the precipitating agents is necessary to the effective and efficient removal of the stroma constituents. If a polyvalent cation and a polysulfate are used alone at low speed centrifugation (below about $10,000 \times g$) inadequate separation is obtained. With high speed centrifugation more stroma is removed but the yield is still not satisfactory and filtration is both difficult and cumbersome. When the polyvalent anion is used a good, packed precipitate is formed on low speed centrifugation and the supernatant can be easily removed and filtered.

In order to further purify the hemoglobin solution if should be filtered and dialyzed. The solution is filtered through a filtration media and the filtrate is dialyzed preferably by passing through a series of artifical kidneys in a manner well-known to those skilled in the art. A final sterile filtration through an 0.2 micron filter may be desirable. Also, if desired any excess sulfate may be removed by precipitation with a divalent cation such as barium or treatment with an ion exchange resin such as DEAE.

The hemoglobin solution so obtained is substantially pure and free of stroma and other lipoprotein cellular constituents along with freedom from noncellular contaminants which tend to degrade the hemoglobin.

In accordance with the present invention, hemoglobin solutions can be prepared which have less than 5% methemoglobin therein and preferably less than 2% methemoglobin therein.

The invention can be further understood with reference to the following examples.

EXAMPLE 1

Outdated human blood cells were charged to a 1 liter centrifuge bottle with an air space allowed thereover. Sterile wash solution consisting of 0.05 moles/liter of $Na_2HPO_4$ and 0.22 moles/liter NaCl is charged at a temperature of 2° to 8° C. to the centrifuge bottles until full. The ratio of wash solution to cells was approximately 1:1. Several such bottles were prepared. The bottles were capped and the wash solution mixed with the blood by inversion. The bottles were placed in a centrifuge and centrifuged at 4,200 rpm ($4,700 \times g$) for 10 minutes. The centrifuge and rotor along with the centrifuge bottles were precooled to 50° C. to prevent methemoglobin formation.

After centrifugation, the supernatent wash solution was aspirated from the bottles. The bottles with the packed cells therein were filled with the same wash solution as above described and mixed by shaking and inversion. Centrifugation and aspiration of supernatant was repeated. The bottles with packed cells therein were filled with cold (2° to 8° C.) sterile 0.85 percent NaCl solution, mixed by inversion, centrifuged and aspirated as previously described. The ratio of sodium chloride solution to cells was 350 ml./unit of cells. The washed cells were poured into a funnel covered with layers of coarse and fine nylon mesh, the coarse nylon mesh having a mesh size of 120 microns and the fine nylon mesh having a mesh size of 40 microns. The nylon mesh retained the clumped white cells and other foreign matter which was present. The red cells were collected in a graduated cylinder in order to measure the amount of reagent required for stroma precipitation.

The pooled cells were disrupted by sonication using an ultrasonic probe equipped with a continuous flow cell. Cold water was passed through the jacket of the cell to avoid excess heating causing the formation of methemoglobin. The cells were pumped through the disruption cell at a speed of 300–350 ml./minute for a total of 5 passes. At the end of the 5 passes the residual cell count was less than or equal to 250,000/cu. mm. The cell lysate, forming a mixture of stroma and cytoplasmic components including hemoglobin, was collected and a 20% solution of calcium chloride was added with agitation thereto. The ratio of calcium chloride solution to cells was 50 ml. calcium chloride/liter of cells. After all of the calcium chloride had been added, the hemoglobin-stroma-calcium chloride admixture was mixed for 10 minutes. Five grams of dextran sulfate/liter of cells was added as a powder to the above admixture and mixed for 30 minutes. After 30 minutes, no undissolved material remained. 0.1 moles of $Na_2H$-

PO$_4$ (in the form of Na$_2$HPO$_4$. 12H$_2$O)/liter of cells was added to the mixture and mixed for 30 minutes. Immediately after the addition of the Na$_2$HPO$_4$ the total admixture was cooled to 2° to 8° C. and allowed to stand overnight (16 hours). The admixture was centrifuged at 4,000 rpm (4,700×g) for 90 minutes. Supernatant hemoglobin solution was collected and the complexed stroma and other lipoprotein constituents remained as the precipitant in the centrifuge bottles.

0.1 mole/liter of solid NaCl was added to the supernatant hemoglobin solution. The solution was passed through a Cuno CPX 90S filter cartridge followed by a Pall AR (0.2 micron). The filtrate was dialyzed by passing it through a series of C-DAK-2.5D artificial kidneys using a countercurrent flow of cold 0.1 molar NaCl solution. Subsequent to dialysis the solution was freed of microbial contamination by passage through a 0.2 micron filter and collected in a sterile bottle. The hemoglobin solution prepared had the following characteristics: 25 percent hemoglobin, 2 percent methemoglobin, and free of microorganisms.

EXAMPLE 2

Example 1 was repeated except that the treatment of the cell lysate with calcium chloride was substituted with a treatment with ferric chloride. The ferric chloride was used as a 0.1 molar aqueous solution and at a ratio of 250 ml. ferric chloride solution to one liter of cells.

The stroma-free hemoglobin produced in accordance with Example 2 was equivalent to the stroma-free hemoglobin of Example 1.

EXAMPLE 3

Example 2 was repeated except that aluminum ammonium sulfate was substituted for ferric chloride with substantially the same results as Example 2.

Thus in accordance with the present invention, a method for preparing stroma-free hemoglobin solution is provided wherein the solution is substantially free not only of stroma but also of other cellular and noncellular lipoproteins, along with a hemoglobin solution which is low in methemoglobin.

The hemoglobin solutions prepared in accordance with the invention can be used as an "in vitro" diagnostic reagent or an "in vivo" blood substitute.

It has been found that the stroma-free hemoglobin solutions in accordance with the invention are useful for the resuscitation of warm blooded animals.

Further, the hemoglobin solutions in accordance with the present invention are extremely stable because of their high purity. The process provided in accordance with the invention allows for the production of stroma-free hemoglobin solutions in large quantities without the need for high speed centrifugation and elaborate purification processes.

Thus although the invention has been described with reference to specific materials and specific processes, the invention is only to be limited as is set forth in the accompanying claims.

We claim:

1. A method of obtaining stroma-free hemoglobin solution from erythrocytes comprising:
   (1) lysing the erythrocytes to form a mixture of stroma and hemoglobin,
   (2) precipitating the stroma from the mixture by treating the mixture with effective amounts of a polyvalent cation, a polysulfate, and a polyvalent anion, and
   (3) separating the supernatant hemoglobin solution from the precipitate.

2. A method of obtaining stroma-free hemoglobin solution from whole blood or blood cells comprising:
   washing the blood to remove noncellular blood components and obtain a mixture of erythrocytes and leukocytes;
   removing leukocytes from the mixture;
   lysing the remaining erythrocytes to form a mixture of stroma and hemoglobin;
   precipitating the stroma from the mixture by treating the mixture with effective amounts of a polyvalent cation, a polysulfate and a polyvalent anion;
   separating the supernatant hemoglobin solution from the precipitate; and
   dialyzing and filtering the hemoglobin solution to obtain a substantially pure hemoglobin solution.

3. The method of claim 1 or 2 wherein said erythrocytes are lysed by mechanical means.

4. The method of claim 1 or 2 wherein the separation is accomplished by low speed centrifugation.

5. The method of claim 1 or 2 wherein the polyvalent cation is a divalent cation.

6. The method of claim 5 wherein said divalent cation is selected from the group consisting of $Ca^{++}$, $Mn^{++}$, $Mg^{++}$, $Ba^{++}$ and $Sn^{++}$.

7. The method of claim 1, 2 or 5 wherein said polyvalent cation is present at a level of 0.025 to 0.20 equivalents of divalent cation/liter in said aqueous solution.

8. The method of claim 1 or 2 wherein said polyvalent cation is provided by calcium chloride.

9. The method of claim 8 wherein said calcium chloride is present at a level of 2.5 to 20 grams/liter of aqueous solution.

10. The method of claim 1 or 2 wherein said polysulfate is dextran sulfate.

11. The method of claim 10 wherein said dextran sulfate is present at a level of 2.5 to 10 grams/liter of said aqueous solution.

12. The method of claim 1 or 2 wherein said polyvalent anion is selected from the group consisting of phosphate, carbonate oxalate and citrate.

13. The method of claim 12 wherein said polyvalent anion is provided by Na$_2$HPO$_4$.

14. The method of claim 1 or 2 wherein excess polysulfate is removed from the hemoglobin solution by precipitation with a divalent cation or treatment with an ion exchange resin.

15. A method of obtaining stroma-free hemoglobin solution from erythrocytes comprising:
   (1) sonicating the erythrocytes to lyse them and form a mixture of stroma and hemoglobin,
   (2) precipitating the stroma from the mixture by treating the mixture with effective amounts of calcium chloride, dextran sulfate and a phosphate anion, and
   (3) separating the precipitate from the supernatant hemoglobin solution by low speed centrifugation.

* * * * *